United States Patent [19]

Lechtken et al.

[11] Patent Number: 4,515,982
[45] Date of Patent: May 7, 1985

[54] AMINOREDUCTONES

[75] Inventors: Peter Lechtken, Frankenthal; Gerhard Mueller, Germersheim; Klaus Schmieder, Frankenthal, all of Fed. Rep. of Germany

[73] Assignee: BASF Aktiengesellschaft, Fed. Rep. of Germany

[21] Appl. No.: 450,097

[22] Filed: Dec. 15, 1982

[30] Foreign Application Priority Data

Dec. 28, 1981 [DE] Fed. Rep. of Germany ....... 3151534

[51] Int. Cl.³ .................. C07C 101/12; C07D 265/36
[52] U.S. Cl. ........................................ 560/125; 96/70; 544/105; 548/344; 548/495; 560/43; 562/452; 562/457; 562/507; 564/191; 564/462
[58] Field of Search .................. 548/344, 495; 560/43, 560/125; 562/452, 457, 507; 564/191, 462; 544/105

[56] References Cited

U.S. PATENT DOCUMENTS 3,239,562 3/1966 Barker .................. 564/447
3,816,137 6/1974 Gabrielsen et al. .................. 96/76
4,371,603 2/1983 Bartels-Keith et al. ............ 430/218

OTHER PUBLICATIONS

Obata et al., C.A. 77, (1972), 3944m.
Obata et al., C.A. 93, (1980), 166 211q.
Cocker et al., J. Chem. Soc., (1950), 2052-2058.

Primary Examiner—Richard L. Raymond
Attorney, Agent, or Firm—Keil and Weinkauf

[57] ABSTRACT

Organic materials which contain from 0.001 to 10% by weight of an aminoreductone I

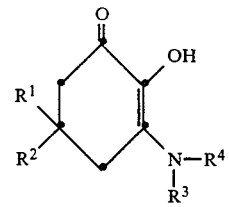

where $R^1$, $R^2$ and $R^3$ are H, methyl or ethyl and $R^4$ is the radical of a naturally occurring α- or β-aminoacid or of a $C_1$–$C_{10}$-alkyl ester thereof or, in the case of an α-aminoacid, a lactone having a 2—OH group in the cyclohexenone ring, or $R^4$ is $C_1$–$C_{20}$-alkyl which is unsubstituted or substituted by —OH, $C_1$–$C_4$-alkoxy or $C_1$–$C_4$-acyloxy, or is —($CH_2$—$CH_2$—O)$_n$H, which may be etherified with a $C_1$–$C_4$-alkanol or esterified with a $C_1$–$C_4$-fatty acid, and where n is from 2 to 10, or a mineral salt thereof.

Novel compounds Ia differ from I in having the radical $R^{4a}$, where $R^{4a}$ is $R^4$ with the exception of methyl. Compounds I are prepared by reacting the corresponding 2,3-dihydroxycyclohex-2-en-1-one with an amine $HN(R^3)R^4$ or a mineral acid salt thereof.

8 Claims, No Drawings

AMINOREDUCTONES

The present invention relates to organic materials containing from 0.001 to 10% by weight of an aminoreductone of the general formula I

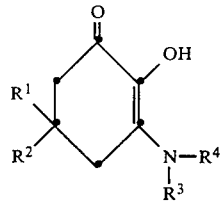

where $R^1$, $R^2$ and $R^3$ are H, methyl or ethyl and $R^4$ is the radical, bonded to a primary amino group, of a naturally occurring α- or β-aminoacid or a $C_1$–$C_{10}$-alkyl ester thereof or, in the case of an α-aminoacid, a radical in which the carboxyl group of the aminoacid and the 2-hydroxyl group of the cyclohexenone ring form a lactone, or $R^4$ is $C_1$–$C_{20}$-alkyl or -alkenyl, which may carry, as substituents, one or more hydroxyl, $C_1$–$C_4$-alkoxy or $C_1$–$C_4$-acyloxy groups, or is —($CH_2$—$CH_2$—O$)_n$H, which may be etherified with a $C_1$–$C_4$-alkanol or esterified with a $C_1$–$C_4$-fatty acid, and where n is from 2 to 10, or a mineral salt thereof, as an antioxidant.

The present invention also relates to the use of the aminoreductones I for stabilizing organic materials against oxidative influences, and to the preparation of these compounds and to the novel aminoreductones of the general formula Ia

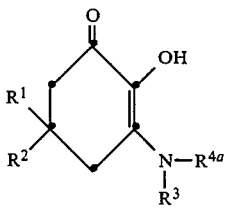

where $R^{4a}$ has the meanings of $R^4$, with the exception of methyl.

In the more general sense, reductones are highly reducing organic substances, chiefly those which are derived from sugars. In the narrower sense, compounds containing the structural element

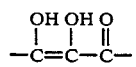

where the hydroxyl groups and the oxygen of the oxo group may also be replaced by the corresponding amine groups, are called reductones.

Reductones, both in the broader and in the narrower sense, have been proposed at various times as antioxidants for organic materials, in particular for foodstuffs, but in this field of use they display non-uniform and even undesirable effects which impair the quality of the foodstuffs, especially that of flavor.

Obata et al. (Nippon Nogei Kagaku Kaishi 45 (11), (1971), 489–495; and C.A. 77 (1972), 3944 m), for example, investigated ascorbic acid (L-3,4-dihydroxy-5-(1,2-dihydroxyethyl)-2,5-dihydrofuran-2-one), triose-reductone (2,3-dihydroxyacrolein), 2,3-dihydroxy-pent-2-en-1-one and some aminoacid derivatives of triose-reductone, of the formula

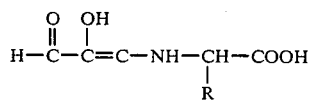

where R is H, methyl, propyl, butyl or mercaptopropyl, and, in a subsequent work (Nippon Nogei Kagaku Kaishi 54 (7) (1980), 542–544; and C.A. 93 (1980), 166 211q), various anils of triose-reductone.

While the aminoacid derivatives of triose-reductone display a better antioxidative effect in soybean oil and cottonseed oil than one of the most familiar standard antioxidants, namely a mixture of 2- and 3-tert.-butyl-4-hydroxyanisole (BHA), the anils are significantly less suitable than BHA for stabilizing lard.

Overall, both works show that the unsubstituted reductones, such as triose-reductone, ascorbic acid and 2,3-dihydroxy-pent-2-en-1-one, are hardly suitable as antioxidants, and also that the antioxidative effect of the amino and imino derivatives of these compounds leaves much to be desired. Apart from this, preparation of these highly sensitive compounds presents serious difficulties.

U.S. Pat. No. 3,816,137 discloses certain 3-amino derivatives of 2,3-dihydroxy-cyclohex-2-en-1-one as photographic developers. These amino derivatives are derived from methylamine, dimethylamine or, chiefly, the heterocyclic amines piperidine and morpholine. These reductones are prepared by reacting the amine in question with 3-chloro-cyclohexane-1,2-dione in the presence of triethylamine. However, this process, which is described in more detail by H. Simon et al. (Chem. Ber. 98 (1965), 3692–3702), is not very suitable for industrial purposes, because of the poor accessibility of the 3-chlorocyclohexane-1,2-diones, and moreover is not uniform when primary amines are used.

Cocker et al., J. Chem. Soc. (1950), 2052–2058, moreover discloses that triose-reductone can be reacted with an aromatic amine or with an α-aminoacid to give the corresponding 3-substitution product of 2,3-dihydroxyacrolein. However, the yields of about 10–36%, based on the triose-reductone, in the case of aminoacids are unsatisfactory.

It is an object of the present invention to stabilize organic materials more effectively than hitherto against oxidative influences, and to provide for this purpose physiologically acceptable antioxidants, most of which are novel and which generally are readily accessible.

We have found that this object is achieved by organic materials containing from 0.001 to 10% by weight of the aminoreductones defined above, which are especially well stabilized against oxidative influences.

We have furthermore found that high yields of the aminoreductones I are obtained in a remarkably smooth reaction between a 2,3-dihydroxycyclohex-2-en-1-one of the general formula II.

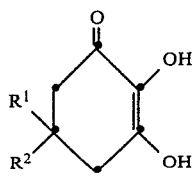

and an amino compound of the general formula III

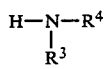

or a mineral acid salt thereof.

Those starting compounds II, in which, preferably, $R^1$ and $R^2$ are both hydrogen, which are not known can be obtained in a conventional manner, for example by the process described in Houben-Weyl, Methoden der organischen Chemie, Volume 6/1d, 266, by hydrogenation of pyrogallol in alkaline solution.

Particularly suitable amino compounds III are those where $R^3$ is hydrogen and $R^4$ is derived from a naturally occurring α- or β-aminoacid having one or more primary amino groups. For the purposes of the invention, naturally occurring aminoacids are, as is generally customary, those which occur in nature as building units, especially of proteins, or as metabolism products. These acids and their $C_1$–$C_{10}$-alkyl esters are physiologically acceptable and thus determine the physiological acceptability of the compounds I, which on metabolism can be broken down first to III and to the reductones II which, according to previous observations, are similarly acceptable, or to oxidation products of these.

Examples of such acids, in which, in the present connection, the configuration is of no importance, ie. they can be used in their optically active forms or, as is usually more economical, in the form of their racemates, are:

Glycine (Gly) 

Alanine (Ala) 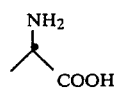

Valine (Val) 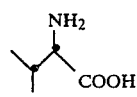

Leucine (Leu) 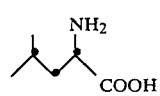

Isoleucine (Ileu) 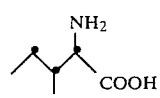

Phenylalanine (Phe) 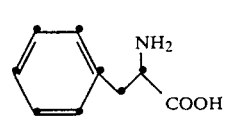

Tyrosine (Tyr) 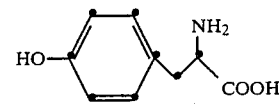

Serine (Ser) 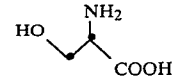

Threonine (Thr) 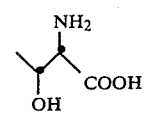

Aspartic acid (Asp) 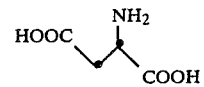

Glutamic acid (Glu) 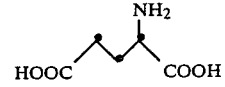

Lysine (Lys) 

β-Alanine 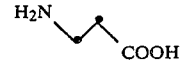

The reaction products of II with the α-aminoacids are either the corresponding free acids Ia or their lactones Ib

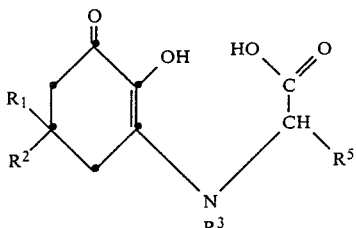

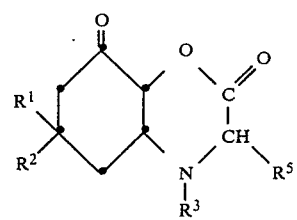

where $R^5$ is the characteristic radical of an α-aminoacid conforming to the above definition.

Since the organic materials to be stabilized are usually organophilic hydrophobic substances, such as oils and fats, it is advantageous to use esters of these acids, because the corresponding compounds I are then compatible with organic materials and can more easily be incorporated into them.

Suitable ester radicals are all those which are derived from straight-chain or branched $C_1$–$C_{10}$-alkanols. The organophilic nature generally, and the fat-solubility particularly, increase as the number of C atoms increases.

Another group of suitable amino compounds III are $C_1$–$C_{20}$-alkylamines and -alkenylamines and N-methyl and N-ethyl derivatives thereof.

Examples of suitable compounds of this type are methylamine, dimethylamine, ethylamine, ethylmethylamine, diethylamine, propylamine, isopropylamine, butylamine, hexylamine, 2-ethylhexylamine, dodecylamine, palmitylamine and stearylamine.

These and the other amines of the type defined can contain hydroxyl groups as substituents, and these can in turn be etherified by means of a $C_1$–$C_4$-alkanol or esterified by means of a $C_1$–$C_4$-fatty acid. The hydroxyl, alkoxy or acyloxy group is preferably in the 2-position relative to the amino group, since the corresponding alkanolamines, for example ethanolamine, aminopropan-2-ol, N-methylethanolamine, aminobutan-2-ol, aminohexan-2-ol and aminododecan-2-ol, can easily be prepared by reacting the corresponding 1,2-epoxy compounds, which in turn are obtainable from the corresponding α-olefins, with ammonia, methylamine or ethylamine.

Amines III which result in particularly good technological properties in the aminoreductones I are those which can be obtained by oxyethylation of ammonia, methylamine or ethylamine, eg.

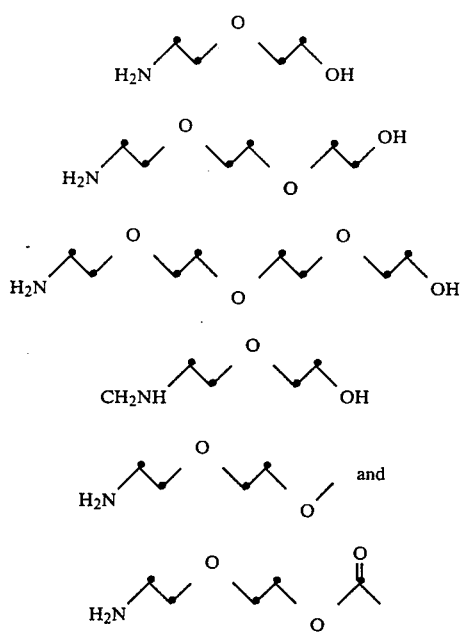

The corresponding compounds I are water-soluble or self-dispersing and can therefore be incorporated in the form of aqueous solutions or dispersions into liquid organic materials and formulations thereof, eg. vitamin formulations.

To prepare the aminoreductones I, 1 mole of II is reacted with from 1 to 3 moles, preferably with an equimolar or approximately equimolar amount, of III, either in bulk or in the presence of a preferably aprotic liquid, such as toluene or xylene, in which the reactants do not have to be dissolved, at from about 30° to 150° C., in particular at from 50° to 120° C. In some cases, the presence of water causes no problems, and in the other cases the water is anyway advantageously removed in the course of the reaction, together with the water formed.

If an α-aminoacid is used, either the open-chain derivative Ia of II or the derivative Ib which has been cyclized to the lactone is obtained. If water is present, the open-chain derivative Ia is predominantly formed, and if the water is removed, the lactone Ib is formed in most cases. Mixtures of Ia and Ib are frequently obtained, and these mixtures can be used, since the two compounds are equivalent in respect of their antioxidative action.

It is advisable to accelerate the reaction by using a catalytic amount of an acid, such as hydrogen chloride or p-toluenesulfonic acid, or an acid ion exchanger, but the reaction also takes place without an acid.

Since both I and II are highly oxidation-sensitive compounds, it is obvious that the reaction must be carried out with strict exclusion of atmospheric oxygen, for example by effecting all operations under nitrogen.

Working up to give the products I is effected in a conventional manner, and further details of this are thus superfluous.

The process products I, which can be prepared by another but less advantageous route, for example from a 3-chloro-2-hydroxy-cyclohex-2-en-1-one and an amino compound III, are novel where $R^4$ is $R^{4a}$, as in substance group Ia.

Preferred novel compounds of this type are those where $R^1$ and $R^2$ are hydrogen and $R^3$ is hydrogen or methyl. Particularly suitable radicals $R^{4a}$ are those of the simple aminoacids Gly, Ala, Val, Leu, Ser, Thr and β-alanine, $C_2$–$C_{10}$-alkylamines and 2-hydroxy derivatives thereof, and amines of the polyether type.

Organic materials which can successfully be stabilized against oxidative influences by means of the compounds I are, in particular, foodstuffs, drugs and animal feeds of all types, in particular fruit juices, oils and fats and oily and fatty formulations. The antioxidants are of particular importance for stabilizing fats which are to be used several times (frying fats) and expensive, highly sensitive substances, such as vitamin A and other compounds of the carotinoid series, or valuable oxidation-sensitive fragrances and aromas.

Plastics which come into contact with foodstuffs are also possible substrates.

The concentration of the antioxidants depends on the required degree of stabilization, and is generally from about 0.001 to 10% by weight. If the substrate is not exposed to extreme influences and is intended for early consumption, concentrations of from 0.001 to 0.05% by weight are sufficient, and in the case of, for example, frying fats from about 0.01 to 1.0% by weight is sufficient. Concentrations of as much as 10% by weight may be advisable only in the case of very sensitive and expensive products, such as vitamins, for which relatively long shelf lives must be allowed for.

The antioxidants according to the invention can be incorporated into the organic materials in a conventional manner, so that further details may be omitted here.

It is noteworthy that the aminoreductones according to the invention are on the one hand highly effective as antioxidants, but on the other hand not so reactive that, according to observations thus far made, they tend to undergo other types of reactions or self-destruction, as is the case with most other compounds of the reductone type.

EXAMPLES

In the text which follows, the radical

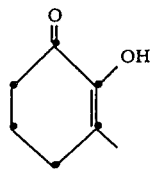

is called radical A. All operations were carried out under nitrogen.

EXAMPLE 1

A—NH—CH₂—COOH 106.5 g (0.83 mole) of A—OH and 75 ml of 2N hydrochloric acid were added to a solution of 150 g (2 moles) of glycine and 450 ml of water, with stirring, and the mixture was heated to the boiling point. At about 40° C., a clear solution was formed, from which the process product started to precipitate out at about 80° C. When the boiling point had been reached, the mixture was cooled to 10° C., and was worked up in a conventional manner to give the precipitate as a yellowish crystalline powder. Recrystallization from hot isopropanol gave an 88% yield of the above aminoreductone in the form of colorless crystals of melting point 185°–187° C.

EXAMPLE 2

A—NH—CH₂—COO—C₂H₅

A mixture of 128 g (1 mole) of A—OH, 149.5 g (1 mole) of glycine ethyl ester hydrochloride, 84 g (1 mole) of NaHCO₃ and 1 liter of toluene was heated at the boil for about 2 hours, with continuous removal of the water of reaction from the system. When the reaction mixture had cooled to 25° C., the NaCl formed was separated off and washed with 1 liter of ethanol. The toluene and ethanol phases were combined and were concentrated at 40° C. under reduced pressure. The residue was recrystallized from 0.2 liter of ethanol, with addition of active charcoal, to give a yield of 60% of colorless crystals of melting point 121°–123° C.

EXAMPLE 3

A—NH—n—C₁₂H₂₅

A mixture of 145 g (0.78 mole) of dodecylamine, 100 g (0.78 mole) of A—OH, 1 g of p-toluenesulfonic acid and 50 ml of toluene was heated at the boil for about 1 hour, while the water of reaction was removed from the system, and 500 ml of n-hexane were then added at 60° C. On further cooling of the mixture, the process product separated out as a yellowish crystal sludge. Recrystallization from n-hexane gave an 81% yield of the pure compound in the form of colorless platelets of melting point 79°–81° C.

EXAMPLES 4 TO 15

A—NR³—R⁴

Various amino compounds HNR³—R⁴ were reacted with A—OH by a method similar to that described in Example 3. The results can be found in Table 1.

TABLE 1

| Example | Compound A—NR³—R⁴ | Melting point °C. | Yield % |
|---|---|---|---|
| 4 | A—NH—CH₂—CH₂—OH | 164–165 | 63 |

TABLE 1-continued

| Example | Compound A—NR³—R⁴ | Melting point °C. | Yield % |
|---|---|---|---|
| 5 | A—NH—CH(CH₃)—COOH | 227–229 | 51 |
| 6 | A—NH—CH₂—CH₂—COOH | 121–123 | 80 |
| 7 | A—NH—CH₂—CH₂—COO—CH₃ | 96–98 | 60 |
| 8 | A—NH—CH₃ | 175–178 | 48 |
| 9 | A—NH—CH₂—CH(CH₃)—OH | 106–107 | 57 |
| 10 | A—N(CH₃)—CH₂—CH₂—OH | liquid | 64 |
| 11 | A—NH—n-hexyl | 101–102 | 70 |
| 12 | A—NH—n-tridecyl | 86–87 | 70 |
| 13 | A—NH—2-ethylhexyl | liquid | 90 |
| 14 | A—N(CH₃)—2-ethylhexy | liquid | 70 |
| 15 | A—NH—(CH₂—CH₂—O)₂H | 85–89 | 52 |

EXAMPLE 16

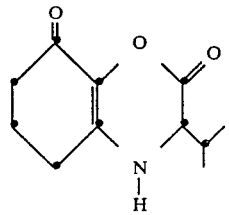

A mixture of 12.8 g (0.1 mole) of A—OH, 12.9 g (0.11 mole) of D,L-valine, 50 ml of toluene and 1 g of p-toluenesulfonic acid was heated at the boiling point for about 2 hours, while the water of reaction was removed from the system. During this time, 3.6 ml (0.2 mole) of water were removed.

The reaction mixture was then cooled, the process product crystallizing out. The crystal mass was separated off and recrystallized from ethanol to give a 57% yield of the pure lactone as colorless crystals of melting point 170°–171° C.

EXAMPLES 17–19

The lactones in Table 2 were prepared from the corresponding starting compounds by a method similar to that described in Example 16.

TABLE 2

| Example | Lactone | Melting point °C. | Yield % |
|---|---|---|---|
| 17 | (structure) | 210–213 | 70 |

TABLE 2-continued

| Example | Lactone | Melting point °C. | Yield % |
|---|---|---|---|
| 18 | 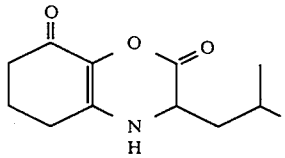 | 165–167 | 55 |
| 19 | 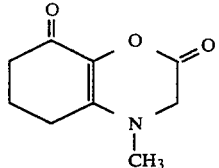 | 133–135 | 52 |

STABILIZING TESTS (a) The stabilizing action of various antioxidants in lard

Lard containing 0.02% by weight of each of various antioxidants was subjected to the so-called peroxide test (for further details, cf. eg. Oil and Soap, 15 (1938), 184). For this, the sample material was stored at 80° C. in the presence of air until it had a peroxide number of 50.

The results of these experiments are summarized in Table 3.

TABLE 3
Peroxide number (PON) of lard

| Experiment | Antioxidant | According to Example No. | Time in days before PON = 50 |
|---|---|---|---|
| Comparative | | | |
| 1 | no additive | — | 1 |
| 2 | ascorbic acid | — | 1 |
| 3 | α-tocopherol | — | 1 |
| 4 | 2,3-dihydroxycyclohex-2-en-1-one (A-OH) | — | 1 |
| 5 | ⅜-tert.-butyl-4-hydroxyanisole (BHA) | — | 2 |
| 6 | ⅜-tert.-butyl-4-hydroxytoluene (BHT) | — | 2 |
| According to the invention | | | |
| 7 | A—NH—n-dodecyl | 3 | 4 |
| 8 | A—NH—CH$_2$—COOH | 1 | 5 |
| 9 | A—NH—2-ethylhexyl | 14 | 7 |
| 10 | A—NH—CH$_2$—CH$_2$—OH | 4 | 9.5 |
| 11 | A—NH—CH$_2$—CH$_2$—COOH | 6 | 10.5 |
| 12 | A—N(CH$_3$)—2-ethylhexyl | 15 | 10.5 |
| 13 | A—NH—CH$_2$—COO—C$_2$H$_5$ | 2 | 10 |
| 14 | A—NH—CH$_3$ | 8 | 12 |
| 15 | 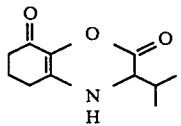 | 16 | 8 |
| 16 | 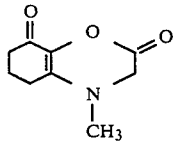 | 19 | 10 |

As can be seen, the antioxidants according to the invention are clearly superior both to other reductone compounds and to other commercially available agents.

(b) Stabilizing action of various antioxidants in dried β-carotine powder

In each case 1.9% by weight of an antioxidant was added to β-carotine powder, and a coating composition was formulated with gelatin in a conventional manner.

The powders were stored at 37° C. in the presence of air for several weeks, during which the β-carotine content was determined at specific intervals of time. The results are summarized in Table 4.

TABLE 4

| Experiment | Antioxidant | According to Example No. | β-carotine content in % of the original content after | | | |
|---|---|---|---|---|---|---|
| | | | 3 | 5 | 8 | 16 |
| | | | weeks | | | |
| Comparative | | | | | | |
| 1 | no additive | — | 14 | — | — | — |
| 2 | α-tocopherol | — | 86 | 80 | 70 | 70 |
| 3 | 3-N—morpholino-5-methyl-2,3-dihydroxy-cyclohex-2-en-1-one | — | 72 | 64 | 60 | 50 |
| According to the invention | | | | | | |
| 4 | A—NH—n-dodecyl | 3 | 91 | 88 | 87 | 82 |
| 5 | A—N(CH$_3$)—2-ethylhexyl | 14 | 88 | 85 | 80 | 80 |

These experiments also show that the agents according to the invention are substantially better than the comparative substances.

(c) Stabilizing action of various antioxidants in dry citranaxanthine powder

Citranaxanthine, which is used as an additive to feed for laying hens, was mixed with 2% by weight of the antioxidant, and the mixture was processed to a dry powder with gelatin in a conventional manner. This powder was then mixed, in a concentration of 20 ppm of active ingredient, with commercially available feed for laying hens, and the feed was stored in the presence of air for 12 weeks, during which the citranaxanthine content was determined every 4 weeks. Table 5 shows the results, which are clearly in favor of the agents according to the invention.

TABLE 5

| Experiment | Antioxidant | According to Example No. | Citranaxanthine content in % of the original content after | | |
|---|---|---|---|---|---|
| | | | 4 | 8 | 12 weeks |
| Comparative | | | | | |
| 1 | no additive | — | 8 | 5 | — |
| 2 | α-tocopherol | — | 13 | 5 | — |
| According to the invention | | | | | |
| 3 | A—NH—dodecyl | 3 | 37 | 36 | 26 |
| 4 | A—NCH$_3$—2-ethylhexyl | 14 | 23 | 20 | 15 |

We claim:
1. An aminoreductone of the formula Ia

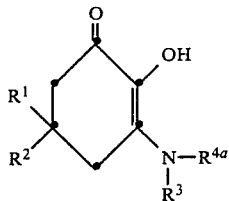

Ia where

R[1], R[2] and R[3] are H, methyl or ethyl, and

R[4a] is the radical, bonded to a primary amino group, selected from the group consisting of a naturally occurring α- or β-amino acid, a $C_1$ to $C_{10}$-alkyl ester thereof, and, in the case of an α-amino acid a radical in which the carboxyl group of the amino acid and the 2-hydroxyl group of the cyclohexenone ring form a lactone, 2-hydroxy-$C_2$ to 10-alkyl, $C_1$ to $C_{20}$-alkenyl, which hydroxy alkyl groups may carry a $C_1$ to $C_4$-alkoxy, or $C_1$ to $C_2$-acyloxy group, or a —($CH_2$—$CH_2$—O)$_n$H group where n is 2 to 10 which group may be etherified with a $C_1$ to $C_4$-alkanol or esterified with a $C_1$ to $C_4$-fatty acid, or a mineral salt thereof.

2. A compound according to claim 1, wherein R[3] is hydrogen and R[4a] is derived from a naturally occurring α- or β-amino acid or a $C_1$ to $C_{10}$-alkyl ester thereof, or in the case of an α-amino acid the carboxyl group of the amino acid and the 2-hydroxyl of the cyclohexenone ring may form a lactone, or a mineral salt thereof.

3. A compound according to claim 1, wherein R[1] and R[2] are hydrogen,

R[3] is hydrogen or methyl, and

R[4a] is a radical of an amino acid selected from the group consisting of glycine, alanine, valine, leucine, serine, threonine and β-alanine, or a mineral salt thereof.

4. A compound according to claim 1, wherein R[1] and R[2] are hydrogen or methyl R[3] is hydrogen or methyl and R[4a] is a 2-hydroxy-$C_2$ to 10-alkyl, or a mineral salt thereof.

5. A compound according to claim 1, wherein R[1] and R[2] are hydrogen,

R[3] is hydrogen or methyl, and

R[4a] is a —($CH_2$—$CH_2$—O)$_n$H group where n is 2 to 10, which group may be etherified with a $C_1$ to $C_4$-alkanol or esterified with a $C_1$ to $C_4$-fatty acid, or a mineral salt thereof.

6. A compound according to claim 2, wherein the compound is

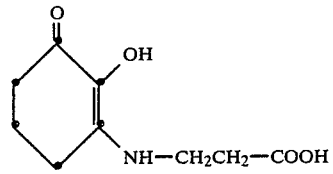

or a mineral salt thereof.

7. A compound according to claim 4, wherein the compound is

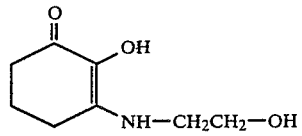

or a mineral salt thereof.

8. A compound according to claim 2, wherein the compound is

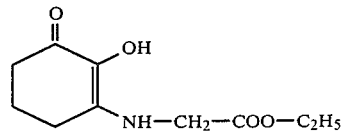

or a mineral salt thereof.

* * * * *